United States Patent
Athalin et al.

(10) Patent No.: US 11,904,037 B2
(45) Date of Patent: *Feb. 20, 2024

(54) ENZYMATIC MOLECULE MIMICKING ANTI-OXIDANT ACTIVITY

(71) Applicant: BIONUCLEI, Aix-en-Provence (FR)

(72) Inventors: Han Athalin, Nantes (FR); Jean-Noël Thorel, Paris (FR)

(73) Assignee: BIONUCLEI, Aix en Provence (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/251,052

(22) PCT Filed: Jun. 3, 2019

(86) PCT No.: PCT/FR2019/051304
§ 371 (c)(1),
(2) Date: Dec. 10, 2020

(87) PCT Pub. No.: WO2019/229402
PCT Pub. Date: Dec. 5, 2019

(65) Prior Publication Data
US 2021/0244635 A1 Aug. 12, 2021

(30) Foreign Application Priority Data

May 31, 2018 (FR) ...................... 1854741

(51) Int. Cl.
*A61K 8/27* (2006.01)
*A23L 33/10* (2016.01)
*A61K 8/34* (2006.01)
*A61Q 17/04* (2006.01)
*A61Q 19/08* (2006.01)

(52) U.S. Cl.
CPC ............... *A61K 8/27* (2013.01); *A23L 33/10* (2016.08); *A61K 8/347* (2013.01); *A61Q 17/04* (2013.01); *A61Q 19/08* (2013.01); *A61K 2800/10* (2013.01); *A61K 2800/413* (2013.01); *A61K 2800/522* (2013.01); *A61K 2800/58* (2013.01); *A61K 2800/622* (2013.01)

(58) Field of Classification Search
None
See application file for complete search history.

(56) References Cited

U.S. PATENT DOCUMENTS

| | | | |
|---|---|---|---|
| 2003/0049287 A1 | 3/2003 | Ley et al. | |
| 2003/0157154 A1* | 8/2003 | Fuller | A61K 31/11 514/699 |
| 2009/0155371 A1 | 6/2009 | Sojka et al. | |
| 2010/0284942 A1 | 11/2010 | Natsch | |

FOREIGN PATENT DOCUMENTS

| | | |
|---|---|---|
| CN | 108084494 A | 5/2018 |
| WO | 2017037731 A1 | 3/2017 |

OTHER PUBLICATIONS

Fabien Grasset, N. Saito, D. Li, D. Park, I. Sakaguchi, et al.. Surface modification of zinc oxide nanoparticles by aminopropyltriethoxysilane. Journal of Alloys and Compounds, Elsevier, 2003, 360 (1-2), pp. 298-311. (Year: 2003).*
Translation of the International Search Report and Written Opinion for International Application No. PCT/FR2019/051304 dated Oct. 14, 2019, 13 pp.
Prathipati, Priyanka et al., "Development of Novel HDL-Mimicking α-tocopherol-coated Nanoparticles to Encapsulate Nerve Growth Factor and Evaluation of Biodistribution," European Journal of Pharmaceutics and Biopharmaceutics, 108, 2010, pp. 126-135.
Arslanoglu, Yasin et al., "Synthesis, Electrochemical and Photophysical Studies of Axially Substituted Quarternizable Titanyl Phthalocyanines," Dyes and Pigments, 97, 2013, pp. 340-346.

* cited by examiner

*Primary Examiner* — Nicole P Babson
(74) *Attorney, Agent, or Firm* — Heslin Rothenberg Farley & Mesiti P.C.

(57) ABSTRACT

Semiconductor colloids grafted covalently with an antioxidant, the colloids being semiconductor colloids constituted by at least one element chosen from the group comprising C, Si, Ge, Sn, S, Se, Te, B, N, P, As, Al, Sb, Ga, In, Cd, Zn, O, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and combinations thereof.

17 Claims, 3 Drawing Sheets

ENZYMATIC MOLECULE MIMICKING ANTI-OXIDANT ACTIVITY

CROSS REFERENCE TO RELATED APPLICATIONS

This application is a national stage filing under section 371 of International Application No. PCT/FR2019/051304 filed on Jun. 3, 2019, and published on Dec. 5, 2019 as WO 2019/229402, which claims priority to French Application No. 1854741, filed on May 31, 2018.

The present invention relates to a complex in the form of an antioxidant grafted onto a reservoir of electrons that is self-regenerated in the presence of photons. It may, in particular, relate to zinc oxide colloids that have been grafted with an antioxidant.

The field of use of such colloids relates in particular to cosmetics, e.g. to sun compositions, anti-age compositions, and food supplements. It may relate to topical protection against the harmful effects of smoking or of a sugar-rich diet, or against the harmful effects induced by exposure to ultraviolet (UV) radiation and/or to pollutant molecules present in the atmosphere.

The skin is an organ that is continuously in renewal and that is subjected to the effects of time. As skin ages, the renewal of its cells slows down. The oldest cells accumulate and give the impression of a dull or cloudy complexion and skin that is off-color, and the skin dries out and becomes thinner. In parallel, modifications in the dermis appear, fatty tissue and muscle tissue wastes away and so support is lost. This is the process of skin ageing.

From a molecular viewpoint, skin ageing is related to a degradation in the cell repair mechanisms. It is determined firstly by an individual "biological clock" that is genetically programmed, and secondly by the capacities of the cell to withstand the oxidative damage caused by toxic substances known as "free radicals". This is ageing that is of intrinsic origin.

In parallel, ageing of extrinsic origin is induced by environmental factors and behaviors that are specific to each individual. By way of example, such extrinsic factors include smoking, natural or artificial atmospheric pollutants, stress, exposure to sun, alcohol consumption, or indeed a sugar-rich diet.

"Natural atmospheric pollutants" means pollutant particles and molecules that are generated by natural activities (volcanoes, ores, oceans, etc.), such as sulfur dioxide or indeed ozone.

"Artificial atmospheric pollutants" means pollutant particles and molecules that are generated by anthropic activities (factories, motor vehicle engines, etc.), such as polycyclic aromatic hydrocarbons (PAHs), heavy metals, or indeed pesticides.

Some such pollutant molecules can cause inflammation, acceleration of cell ageing, or even certain skin cancers. Among such compounds, persistent organic pollutants (POPs) are some of the atmospheric pollutants that are most dangerous for health. They generally bind to the surface of the skin. After they are absorbed, an oxidative stress phenomenon takes place that causes the acceleration in the skin ageing process.

Similarly, UV radiation leads, in particular, and directly or indirectly, to appearance of an imbalance between pro-oxidants and antioxidants, resulting in appearance of a phenomenon of oxidative stress in cells, e.g. in the cells of the skin.

A sugar-rich diet can lead to appearance of glycated proteins that can be neither destroyed nor released from the cell. That results in increased production of free radicals that generates an imbalance in favor of pro-oxidant activity and thus in favor of physiological ageing of the human organism.

Alcohol consumption and/or tobacco smoking modifies the metabolism of the cells and increases the production of free radicals, thereby generating an imbalance between the quantity of such free radicals that are produced and the antioxidant defense system.

A free radical may be defined as a chemical species (molecule or atom) that has one or more unpaired electrons on its outer layer. The most frequent free radicals are hydroxyl radicals (OH·), superoxides ($O_2·^-$), nitric oxides (NO·), thiols (RS·), or indeed peroxyls ($RO_2·^-$). If the free radical corresponds to an oxygen, the radicals are referred to as "reactive oxygen species" or "ROS", such as singlet oxygen ($^1O_2$) or indeed the superoxide anion ($O_2·^-$).

Free radicals are chemical molecules that are unstable due to the unpaired electrons that make them very reactive to the surrounding molecules. A free radical is a pro-oxidant that is neutralized to the detriment of the adjacent molecule, which, in turn becomes a free radical, and so on. The phenomenon is propagated by chain reactions, and this constitutes oxidative stress.

In practice, each pro-oxidant molecule requires at least one electron or indeed two or three electrons to be added in order to be stabilized, i.e. in order to be neutralized.

The skin is faced with attack from the surrounding environment on a daily basis. To defend itself against such attacks, the human body has developed defense systems using enzymatic and/or non-enzymatic antioxidants. However, when an excessive quantity of free radicals is generated, an imbalance is established and the antioxidant defense system finds itself overwhelmed, leading to damage being caused to the skin tissue.

Antioxidants can be defined as being any substance that, when present at a low concentration relative to the oxidizable substrate, is capable of at least slowing down the oxidation of the substrate.

That functional definition applies to a large number of substances, including not only enzymes having specific catalytic properties, but also small hydrophilic or fat-soluble molecules. This great physical and chemical variety allows antioxidants to be present in all compartments of the human organism, be they intracellular, membranous, or extracellular.

By way of example, enzymatic antioxidants include superoxide dismutase or glutathione peroxidase, and non-enzymatic antioxidants include vitamins (A, C, E), trace elements (selenium) or indeed proteins (ferritin).

The activity of antioxidants makes it possible to slow down, delay, or prevent the pro-oxidant chain reaction initiated by free radicals. They are thus prevention or termination agents that are capable of avoiding or of trapping free radicals. In other words, antioxidants transform radicals into compounds that are more stable and inhibit the phase of propagation via multi-electron transfer to pro-oxidant elements so as to stabilize them partially or completely.

The complex of the invention has antioxidant activity that mimics the antioxidant activity of superoxide dismutase (SOD).

The activity of SOD corresponds to a catalytic activity of dismutation of the superoxide anion ($O_2·^-$), into dioxygen ($O_2$) and hydrogen peroxide ($H_2O_2$). The products of this reaction are considered to be oxygen free radicals even though they do not have unpaired electrons, and they are highly reactive and harmful. By way of example, in the presence of iron, hydrogen peroxide decomposes and produces a hydroxyl radical OH· that is highly toxic for most organic structures. Such products are then considered to be secondary ROS that are produced by the reaction of dismutation of the superoxide anion.

Under physiological conditions, such dismutation is slow and leads to an extended half-life of the superoxide anion, producing harmful oxidation of the biological macromolecules by production of said secondary ROS. Unfortunately, the toxicity of such ROS is considerably greater than that of the superoxide anion.

SOD catalyzes and therefore accelerates the dismutation of the superoxide anion so as to reduce its half-life and thus so as to limit the pro-oxidant effects of the ROS produced secondarily to the reaction of the dismutation of the superoxide anion.

Furthermore, SOD also makes it possible to eliminate other ROS, e.g. $^1O_2$ or ROO.

Indeed, SOD is an enzyme that is capable of reducing a pro-oxidant by multi-electron transfer. In other words, SOD can react with all of the ROS so as to stabilize them and prevent or neutralize their pro-oxidant activity.

That protein therefore provides a catalytic activity that is essential to the mechanism for eliminating ROS and therefore for eliminating oxidative stress.

In cosmetics, numerous products are designed to produce an antioxidant effect, also known as an "anti-radical" effect, for combating ageing of intrinsic origin and/or of extrinsic origin.

Protection against oxidative stress, induced, in particular, by extrinsic factors, is currently based on using the antioxidant virtues of plant extracts, for example. However, such formulations are complex, and they use a very large number of ingredients, including, among others, solvents and preservatives, the innocuity of which is not always established in the short or long terms.

Therefore, and despite their formulations, it appears that the effectiveness of the vast majority of the solutions proposed is not sufficient.

Derivatives of antioxidant molecules are used more commonly in pharmaceutical formulations. However, they suffer from the drawback of being less effective and less available compared with antioxidants in the native state and at equivalent doses.

Conventional solutions for combating free radicals and their consequences require frequently repeated application in order to provide a protective and/or reparative effect that is uniform and continuous over time.

Currently, no cosmetic composition proposes a formulation that includes an enzymatic molecule that has activity that is stable over time, for oxidizing all types of ROS and for reducing or eliminating oxidative stress.

To solve this problem, the Applicant has developed a complex that mimics the effect of SOD.

This complex results from combining an antioxidant and colloids, serving as an electron reservoir, thereby making it possible to combat the harmful effects of all of the free radicals.

More specifically, the present invention relates to semiconductor colloids that are grafted covalently, i.e. via at least one covalent bond or spacer arm, with an antioxidant.

These semiconductor colloids are advantageously constituted by at least one element chosen from the group comprising C, Si, Ge, Sn, S, Se, Te, B, N, P, As, Al, Sb, Ga, In, Cd, Zn, O, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and combinations thereof.

In advantageous manner, the semiconductor colloids of the invention comprise two or three of these elements.

In a particular implementation, the semiconductor colloids of the invention are colloids of zinc oxide, ZnO. In a particular implementation, the semiconductor colloids of the invention are colloids of rutile titanium dioxide, $TiO_2$.

In a particular implementation, the semiconductor colloids of the invention are colloids of bismuth oxide, $Bi_2O_3$.

In general, the term "semiconductor colloid" means a compound having an energy difference between the valence band and the conduction band that is small enough for one electron to go from one to the other.

In the meaning of the invention the term "antioxidant" designates an organic molecule capable of giving at least one electron or H· to a chemical species. In accordance with the invention, this antioxidant carries at least one function capable of reacting with an available function present at the surfaces of the semiconductor colloids to create the complex of the invention.

The antioxidant is grafted by formation of one or more covalent chemical bonds, referred to below as "spacer arm(s)" or "precursor(s)", between the colloids and the antioxidant.

The complex of the invention comprises 2 elements, namely a colloid and an antioxidant that are bonded together by a covalent bond. The colloid acts as an electron reservoir, i.e. due to its proximity it is capable of transferring an electron to the antioxidant, and of doing so as long as the reservoir contains electrons and as long as the antioxidant is seeking electrons. The electron transferred in this way makes it possible to regenerate the anti-radical function of the antioxidant. The complex of the invention thus has an activity that mimics the activity of SOD, i.e. it is capable of reducing a pro-oxidant by means of a plurality of electrons.

In accordance with another characteristic, for topical application, and subject to exposure to electromagnetic radiation, e.g. to ultraviolet (UV) rays, in particular in the range 280 nm to 400 nm in the UV-A and UV-B range, the colloid is electronically regenerated by conversion of the photonic energy into electrons. This means that the reservoir has the capacity to give electrons to the antioxidant indefinitely.

In summary, the colloids constitute a reservoir of electrons making it possible to regenerate the anti-radical activity of the antioxidant that can then react with as many free radicals as there are electrons available in the colloids and/or oxidize and thus neutralize all of the radical compounds. This effect is related to the proximity between the colloids and the antioxidant. Indeed, in the absence of grafting, the antioxidant, AntiOx, is not regenerated even when colloids are present in the reaction medium.

In general, colloids, also referred to as "Col", are crystalline particles (non-amorphous form) having semiconductor properties resulting from the ordered stack of molecules, e.g. molecules of ZnO. Such colloids may also be called "quantum dots" or "nanocrystals". They may also be in the form of a dispersion or of a suspension, and advantageously of a dispersion, of colloids in an aqueous medium.

The colloids may be synthesized using conventional techniques, e.g. by a "bottom-up" approach of growing precursors. This type of synthesis, commonly used in the field of nanomaterials, implements a step of nucleation and a step of growth from isolated atoms. It makes it possible to control the size of the colloids at the nanometric scale.

For greater clarity, the term "Col/AntiOx" is used to designate the colloids of the invention, i.e. colloids, e.g. of zinc oxide, grafted with an antioxidant. Furthermore, "AntiOx" designates the antioxidant grafted to the colloids.

The concept of grafting, or of functionalization, of colloids is part of the general knowledge of the person skilled in the art. Grafting, or functionalization, corresponds to formation of covalent bonds between the antioxidant and the surfaces of the colloids. Grafting the antioxidant to the colloid via a spacer arm positioned between the semiconductor colloid and the antioxidant, imparts the proximity necessary for the multi-electron transfer from the colloids to the antioxidant.

Col/AntiOx colloids offer the advantage of imparting an antioxidant effect that is self-regenerating in the presence of organic molecules, e.g. in the presence of organic radicals or free radicals.

Advantageously, the grafted antioxidant AntiOx is stabler. In other words, the half-life of the antioxidant AntiOx is increased.

The presence of the Col/AntiOx colloids makes it possible to avoid formation of radical species secondary to the reaction, in particular singlet oxygen and/or hydrogen peroxide. Conversely, the prior art compositions do not block formation of secondary radical compounds, which is translated by formation of an imbalance between pro-oxidants and antioxidants, producing a "secondary" oxidative stress and cell damage.

In other words, the Col/AntiOx colloids of the invention neutralize any primary and/or secondary pro-oxidation activity.

In general, the colloids have a mean size in the range a few nanometers to a few tens of nanometers.

Thus, the colloids have a size lying advantageously in the range 0.5 nm to 1000 nm, more advantageously in the range 10 nm to 100 nm, and even more advantageously about 30 nm, the size being measured by XRD.

The XRD (X-ray diffraction) technique is a technique conventionally used for measuring the size of crystals in the solid state.

The term "size" means the largest dimension of the colloids (Col or Col/AntiOx), e.g. the diameter when the colloids are of spherical shape. It is the mean size of the grafted colloids (Col/AntiOx) or of the non-grafted colloids (Col). Indeed, the size of the grafted colloids Col/AntiOx generally lies in the ranges of values given above. Where necessary, the person skilled in the art is capable of adapting the size of the non-grafted colloids Col.

The colloids Col and/or Col/AntiOx are advantageously of spherical shape.

Naturally, the grafting is not limited to grafting a single molecule of a single antioxidant to a colloid. It is grafting of a multitude of molecules of at least one type of antioxidant AntiOx to each nanocrystal, e.g. of zinc oxide.

The antioxidant AntiOX is a molecule capable of giving at least one electron. It may, in particular, be chosen from the group of compounds comprising at least one hydroxyl group (—OH) over at least one aromatic cycle.

Advantageously, the antioxidant AntiOx is a phenol, i.e. a phenyl having at least one hydroxyl group (—OH), or at least one of its derivatives or complexes thereof.

The antioxidant AntiOx may, in particular be chosen from the group comprising the compounds or their derivatives designated by the following International Nomenclature of Cosmetic Ingredients (INCI) names: octadecyl di-t-butyl-4-hydroxyhydrocinnamate; pentaerythrityl tetra-di-t-butyl hydroxyhydrocinnamate; 2,6-Bis(1,1-dimethylethyl)-4-methylphenol; bis-ethylhexyl hydroxydimethoxy benzylmalonate; manganese dioxide; colloidal platinum; tert-butylhydroquinone; tetrabutyl ethylidenebisphenol; sodium bisulfite; sodium metabisulfite; thioglycolic acid; thiotaurine; thioctic acid; dilauryl thiodipropionate; aminoethanesulfinic acid; triethyl citrate; sodium erythorbate; sorbityl furfural; erythorbic acid; perillyl alcohol; pyridyloxide t-butylnitrone; ergothioneine; melatonin; acetyl cysteine; cysteine; lysine hydrochloride; carnosic acid; tyrosyl histidine HCl; histidine hydrochloride; pyridoxine serinate; superoxide dismutase; aminopropyl ascorbyl phosphate; ascorbic acid; ascorbic acid polypeptide; ascorbyl dipalmitate; ascorbyl glucoside; ascorbyl linoleate; ascorbyl methylsilanol pectinate; ascorbyl palmitate; ascorbyl tetraisopalmitate; ascorbyl tocopheryl maleate; trisodium ascorbyl palmitate phosphate; disodium ascorbyl sulfate; calcium ascorbate; methylsilanol ascorbate; sodium ascorbate; sodium ascorbyl phosphate; sodium ascorbyl/cholesteryl phosphate; tetrahexyldecyl ascorbate; magnesium ascorbyl phosphate; tocopherol; tocopheryl acetate; tocopheryl linoleate; tocopheryl linoleate/oleate; tocopheryl nicotinate; tocopheryl retinoate; sodium tocopheryl phosphate; dioleyl tocopheryl methylsilanol; potassium ascorbyl tocopheryl phosphate; dodecyl gallate; epigallocatechin gallate EGCG; propyl gallate; ethyl ferulate; ethylhexyl ferulate; chitosan ascorbate; chitosan glycolate; apigenin; tiliroside; alpha-arbutin; arbutin; baicalin; quercetin; quercetin caprylate; isoquercetin=isoquercitrin; isoquercitrin; diethylhexyl syringylidenemalonate; dihydroxy methylchromone; dimethoxy di-p-cresol; dimethylmethoxy chromanol; ethylbisiminomethylguaiacol manganese chloride; hesperidin methyl chalcone; kojic acid; kojic dipalmitate; madecassoside; asiaticoside; magnolol (5,5'-diallyl-2,2'-dihydroxybiphenyl); nordihydroguaiaretic acid; phenylethyl resorcinol; resveratrol; troxerutin (3',4',7-tris(hydroxyethyl)rutin); glucosylrutin; rutin (4H-1-benzopyran-4-one); disodium rutinyl disulfate; tetrahydrobisdemethoxydiferuloylmethane; tetrahydrodemethoxydiferuloylmethane; tetrahydrodiferuloylmethane; tococysteamide; totarol; hydroxydecyl ubiquinone; ubiquinone=coenz Q 10; carotenoids; lycopene; gallic acid; and caffeic acid.

In a particular implementation, the colloid is a ZnO or $TiO_2$ colloid, and the AntiOx has an aldehyde group (—CHO) or an acid group capable of reacting with the available functions of the spacer arm providing the covalent bond with the surfaces of said colloids Col. In a particular implementation, the antioxidant is a phenolic aldehyde or a phenolic acid.

By way of example, the antioxidant AntiOx is, in this situation, 2-hydroxybenzaldehyde 3-hydroxybenzaldehyde, 4-hydroxybenzaldehyde, 3,4 dihydroxybenzaldehyde, 2,3 dihydroxybenzaldehyde, 4,5 dihydroxybenzaldehyde, and advantageously 3-hydroxybenzaldehyde or 3,4 dihydroxybenzaldehyde (protocatechuic aldehyde).

Advantageously, and also in this implementation, the spacer arm comprises in the range 1 to 8 carbons, and preferably in the range 2 to 4 carbons, and has an alkoxysilane function capable of binding itself covalently to the colloid and a function of the hydroxyl type, of the phosphate type, or of the amine type capable of binding itself to the antioxidant.

Advantageously, the spacer arm is a derivative of silica, advantageously an alkoxysilane, and even more advantageously it is 3-(Aminopropyl)triethoxysilane.

Advantageously, the ratio of the colloid to the silica derivative used for forming the spacer arm lies in the range 1/1 to 10/1, and preferably in the range 2/1 to 3/1.

Naturally, the spacer arm is chosen as a function of the nature of the antioxidant so as to provide the covalent bond, and so that the proximity between Col and AntiOx is sufficient to enable the multi-electron transfer to take place from the colloids to the antioxidant.

Advantageously, the colloids grafted with an antioxidant of the invention are ZnO or $TiO_2$ colloids grafted with 3-hydroxybenzaldehyde.

The covalent grafting of the antioxidant AntiOx is performed conventionally by reaction between a function of the antioxidant AntiOx or a precursor of the antioxidant AntiOx and available functions at the surfaces of the colloids Col.

The colloids are not doped. Optionally, they may include a transition metal that is introduced during synthesis of the colloids.

The term "doping" means incorporation of an element into a material that is already formed. Incorporating an element while a material is being synthesized, i.e. upstream from the formation of the material, is not considered as being doping.

The present invention also provides the use of colloids grafted with at least one antioxidant.

The colloids Col/AntiOx may be used in a topical composition, e.g. a cosmetic composition, but also in a cosmetic composition for non-therapeutic use. This composition is advantageously hydrophilic, micellar or a Pickering emulsion (a reverse form of a micellar composition).

When the composition is for topical use, the formulation is advantageously devoid of sun filters, be they lipophilic or hydrophilic, or inorganic or organic. Their presence would lead to preventing passing of the UV necessary and essential for obtaining the antioxidant effects and self-regenerating effects as described.

The cosmetic composition of the invention may further include the additives that are usual in the field in question.

Naturally, the person skilled in the art will be watchful to choose any such additives or supplementary excipients, and/or their quantities, in a manner such that the advantageous properties of the composition of the invention are not, or are only slightly, degraded by the addition being considered.

The colloids Col/AntiOx may also be used in a food supplement, e.g. a probiotic.

When the complexes are used as a food supplement, the antioxidant is regenerated only up to the electron content of the reservoir, i.e. of the colloid. Indeed, in such a situation, the colloids are not exposed to ultraviolet radiation, which prevents them from being regenerated. Conversely, the antioxidant AntiOx has available to it the reservoir of electrons constituted by the colloids, thereby increasing its half-life and its effectiveness.

The food supplement including Col/AntiOx may also include conventional excipients. In particular, it may be in the form of capsules or of tablets.

The invention and the advantages resulting from it appear more clearly from the following figures and examples that are given to illustrate the invention and in non-limiting manner.

EXAMPLES OF IMPLEMENTATIONS OF THE INVENTION

Example 1: ZnO/3-hydroxybenzaldehyde

1/ Synthesis of the Colloids

The percentages are given by weight of the composition.

A zinc oxide precursor, such as anhydrous zinc acetate (2%) and sodium hydroxide (1.5%), was mixed with a solvent or with a mixture of solvents comprising ethanol (85%) and diethylene glycol (8%) and sealed in an autoclave. The solvent may also be benzyl alcohol, phenol, oleyl alcohol, butanol, propanol, isopropanol, water, tetrahydrofuran, ethanol, methanol, acetonitrile, toluene, PGMEA, PGPE, PGME, 2-methyl-1-propanol, or triethylene glycol monomethyl ether.

The reaction medium was placed under mechanical agitation at 60° C. for about 30 minutes, until the salts had dissolved. Water (2%) was then added. Cloudiness was observed that marked the start of formation of the particles. The reaction was kept at 65° C. for one and a half hours.

Zinc oxide nanocrystals that were spherical and 7 nm in diameter were collected.

2/ Preparation of the Colloids Col/AntiOx

Colloids of the invention were prepared using the zinc oxide (ZnO) colloids obtained above and a precursor or spacer arm of the antioxidant 3-hydroxybenzaldehyde. Particles of ZnO/3-hydroxybenzaldehyde were thus obtained. In practice, the nanocrystals formed were functionalized in situ with (3-Aminopropyl)triethoxysilane (0.5%). On addition, the solution cleared slightly. This functionalization was performed for an additional 3 hours. Finally the antioxidant 3-Hydroxybenzaldehyde (1.5%) was added. The reaction was maintained for 9 hours.

The reactor was then cooled to ambient temperature. The particles were collected and centrifuged at 3000 rpm for 15 minutes. They were then washed in ethanol, and then centrifuged again. Finally, the particles were dispersed to the desired concentration in water (mass concentration in the range 10% to 15%).

The small size of the ZnO particles made it possible to have a larger area to cover and thus to graft a larger number of antioxidant molecules to the surface of each of the particles.

The diameter of the ZnO colloids was measured by means of an X-ray diffractometer (XRD). The wavelength produced by the diffractometer corresponded to the Cu-Kα line equal to 1.54 Å. The other parameters used corresponded to an acceleration voltage of 40 kV, to an electric current of 40 mA, and to a Bragg-Brentano geometry.

Figure 1:
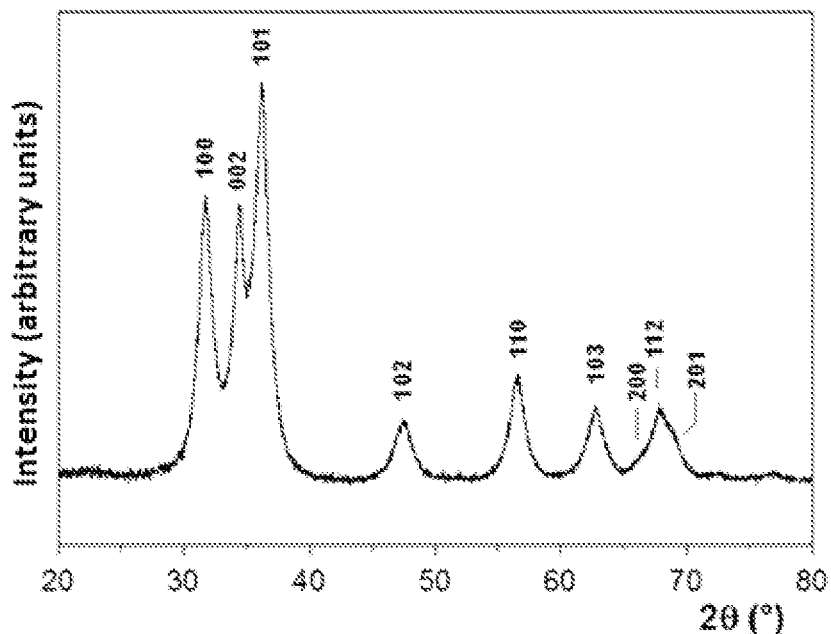
FIG. 1 shows the X-ray diffraction pattern of ZnO colloids after functionalization with the antioxidant. The spectrum lines are indexed with the planes corresponding to the hexagonal ZnO structure.

The X-ray diffraction patterns were measured on powder with an XRD of Cu-Kα source in transmission. The X-ray diffraction pattern of colloids before functionalization (grafting) with the antioxidant is shown in FIG. 1.

Example 2: TiO$_2$/3-hydroxybenzaldehyde

Under the same conditions as in the preceding example, the same antioxidant was grafted onto rutile titanium dioxide. 5 g of rutile titanium dioxide was dispersed in a mixture of 950 mL ethanol and 50 mL diethylene glycol. The mixture was heated to 65° C. and agitated. 5 mL of water was added, and then 8 mL of (3-Aminopropyl)triethoxysilane. The mixture was left to be agitated for two hours, and then 5 g of 3-hydroxybenzaldehyde was added, and the mixture was left to be agitated and heated at 65° C. for 9 hours. The mixture was then cooled to ambient temperature. The particles were collected and centrifuged at 3000 rpm for 15 minutes. They were then washed in ethanol, and then centrifuged again. Finally, the particles were dispersed to the desired concentration in water.

Similar syntheses may be performed by implementing as 2-hydroxybenzaldehyde or 4-hydroxybenzaldehyde as antioxidant.

Example 3: TiO$_2$/3,4 dihydroxybenzaldehyde

Under the same conditions as in the preceding example, the 3,4 dihydroxybenzaldehyde was grafted onto rutile titanium dioxide. 5 g of rutile titanium dioxide was dispersed in a mixture of 950 mL ethanol and 50 mL diethylene glycol. The mixture was heated to 65° C. and agitated. 5 mL of water was added, and then 8 mL of (3-Aminopropyl)triethoxysilane. The mixture was left to be agitated for two hours, and then 5 g of 3,4 dihydroxybenzaldehyde was added, and the mixture was left to be agitated and heated at 65° C. for 9 hours. The mixture was then cooled to ambient temperature. The particles were collected and centrifuged at 3000 rpm for 15 minutes. They were then washed in ethanol, and then centrifuged again. Finally, the particles were dispersed to the desired concentration in water.

Example 4: Comparison of the Kinetic Time of the Antioxidant Activity of the Colloids Col/AntiOx (ZnO/3-hydroxybenzaldehyde) with that of a Free Antioxidant (ZnO/3-hydroxybenzaldehyde)

The rate of action of the colloids Col/AntiOx was estimated by measuring the decomposition kinetics of 2,2-diphenyl-1-picrylhydrazyl (DPPH).

DPPH is a molecule that keeps its free radical capacity stably. This radical species absorbs light at 520 nm (purple color of the solution) and becomes colorless or pale yellow after neutralization by an antioxidant. It is thus possible to monitor the neutralization reaction by measuring the intensity of the measurement of absorption of the radical DPPH as a function of time.

For that purpose, two solutions in ethanol were prepared as follows:
- a control solution containing DPPH at a [DPPH]$_0$ concentration of 0.1 mol/L; and
- a test solution containing DPPH at a [DPPH]$_0$ concentration of 0.1 mol/L and an antioxidant at a concentration such that 90% of the DPPH was consumed after 2 hours (as determined based on the CI$_{50}$ measurements).

Absorbance was measured by means of a UV/vis/NIR spectrometer. 2.5 mL of solution was poured into a polystyrene vessel (optical path=1 cm). The UV/visible absorption spectrum from 310 nm to 700 mm was measured for 300 seconds. The value of the absorbance at 520 nm made it possible to determine the concentration of radical DPPH at a given time using the Beer-Lambert equation:

$$A_{520\ nm}(\tau) = \varepsilon_{DPPH} \cdot l \cdot [DPPH]_\tau$$

In accordance with that equation, A corresponds to the measured absorbance, $\varepsilon_{DPPH}$ corresponds to the mass coefficient of DPPH, 1 (cm) corresponds to the optical path through the sample, and [DPPH]$_\tau$ (g/L) corresponds to the mass concentration of the sample.

The curves obtained were honed using a kinetic model that made it possible to go back to the reaction rate or "kinetic" constant K and the half-life constant z of the reaction.

Figure 2:
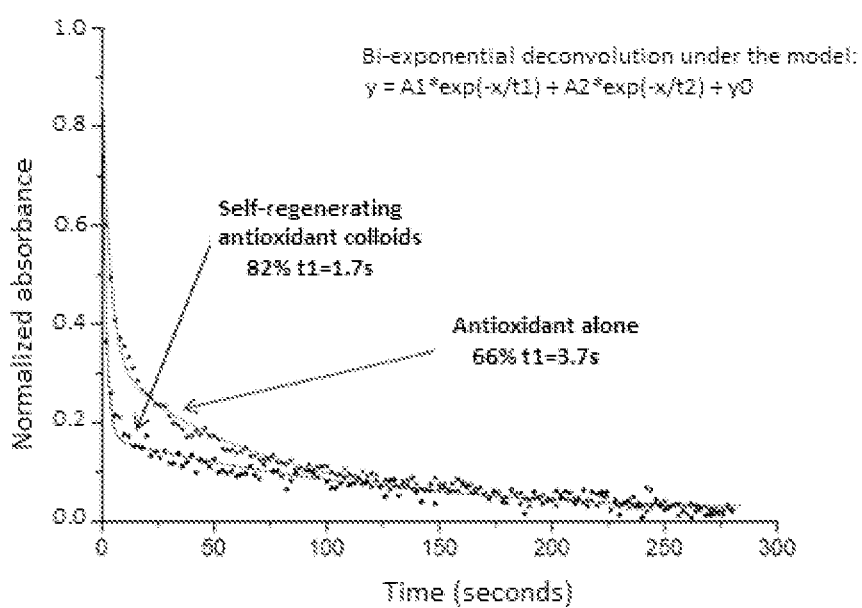
FIG. 2 shows the DPPH kinetics for colloids functionalized with the antioxidant (Col/AntiOx) and for the antioxidant alone.

The graph showing the rate of action of the colloids functionalized with an antioxidant (ZnO/3-hydroxybenzaldehyde) and the rate of action of the free, i.e. not grafted, antioxidant (3-hydroxybenzaldehyde) is shown in FIG. 2.

The results show that the ZnO/3-hydroxybenzaldehyde antioxidant reacts more quickly with DPPH than the free 3-hydroxybenzaldehyde.

Example 5: Assessing the Regeneration of the Antioxidant Activity of the Col/AntiOx Colloids 5.1/ Assessment Over Time A stock solution of ABTS (2,2'-azino-bis(3-ethylbenzothiazoline-6-sulfonic) acid) at 8 mM was incubated, at equal volume, with a solution at 3 mM comprising metmyoglobin and hydrogen peroxide so as to produce an ABTS radical cation. The solution obtained was diluted with phosphate buffer (0.2 M, and pH 7.4) containing 150 mM of NaCl so as to obtain an absorbance of 1.5 at 734 nm.

Samples of 30 μL of ZnO/3-hydroxybenzaldehyde (example 2/) dispersed at 240 g/L in water were added to 2970 μL of the 0.07 mM ABTS cation solution in water, and then placed under agitation in the dark.

After 30 minutes of incubation, the ABTS was totally degraded.

The solution obtained after this step of degradation of the entire ABTS substrate was separated: a fraction of the solution being placed in the dark, and the remaining fraction being placed under UV irradiation. After 30 minutes of exposure (in the dark or under UV), 30 μL of a concentrated solution of ABTS (7 mM) was added, and then the solutions were, once again, placed in the dark under agitation for 5 hours. The absorption was then measured every 30 minutes.

Figure 3:
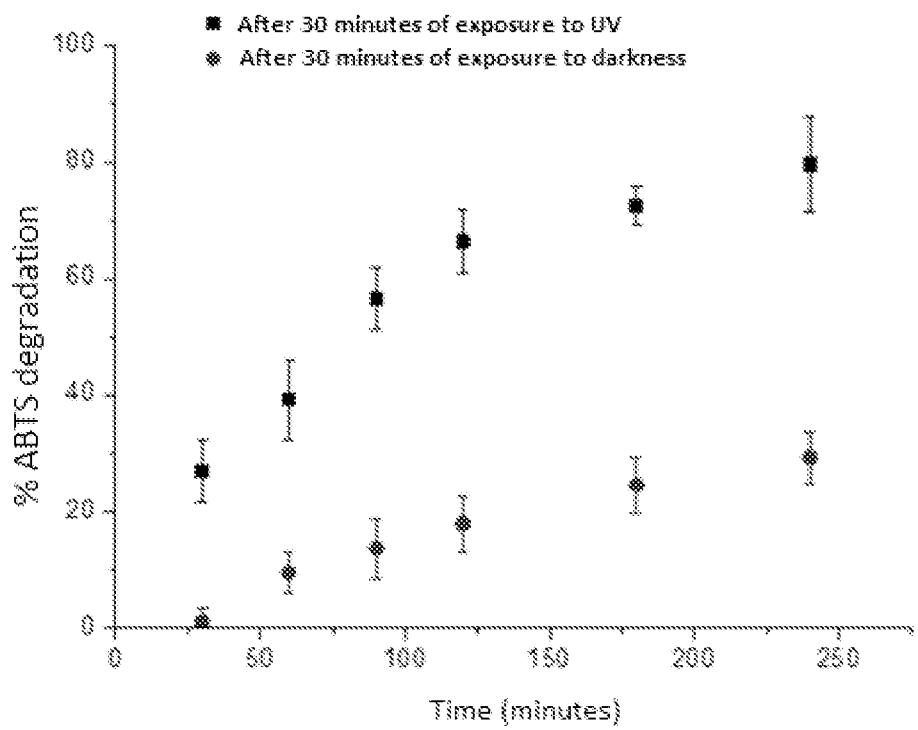
FIG. 3 shows the percentage of ABTS substrate degraded by the colloids of the invention as exposed to UV rays or as kept in the dark.

The data is shown in FIG. 3.

The results show that the solution containing ZnO/3-hydroxybenzaldehyde colloids and exposed to UV radiation has an ABTS degradation capacity that is considerably greater than the solution containing ZnO/3-hydroxybenzaldehyde colloids that remained in the dark. The ABTS degradation activity observed for the solution placed in the dark corresponds to the residual anti-radical activity inherent to the ZnO/3-hydroxybenzaldehyde complex. Thus, after 120 minutes, 65% of the ABTS was degraded by the solution that had been exposed to UV radiation, as compared with 18% for the solution that remained in the dark.

In conclusion, the ZnO/3-hydroxybenzaldehyde colloids of the invention have the capacity to regenerate their antioxidant activity when they are exposed to UV radiation.

5.2/ Comparison with Tocopherol.

The protocol for preparing the solutions as in point 4.1/ was repeated with a concentration of ZnO/3-hydroxybenzaldehyde colloids of 0.5 g/L and a concentration of tocopherol of 1.5 g/L.

The solutions obtained were separated: a fraction of the solution being placed in the dark, and the remaining fraction being placed under UV irradiation. After 30 minutes of exposure (to the dark or to UV), 30 µL of a concentrated solution of ABTS (7 mM) was added, and the absorption was then measured.

Figure 4:
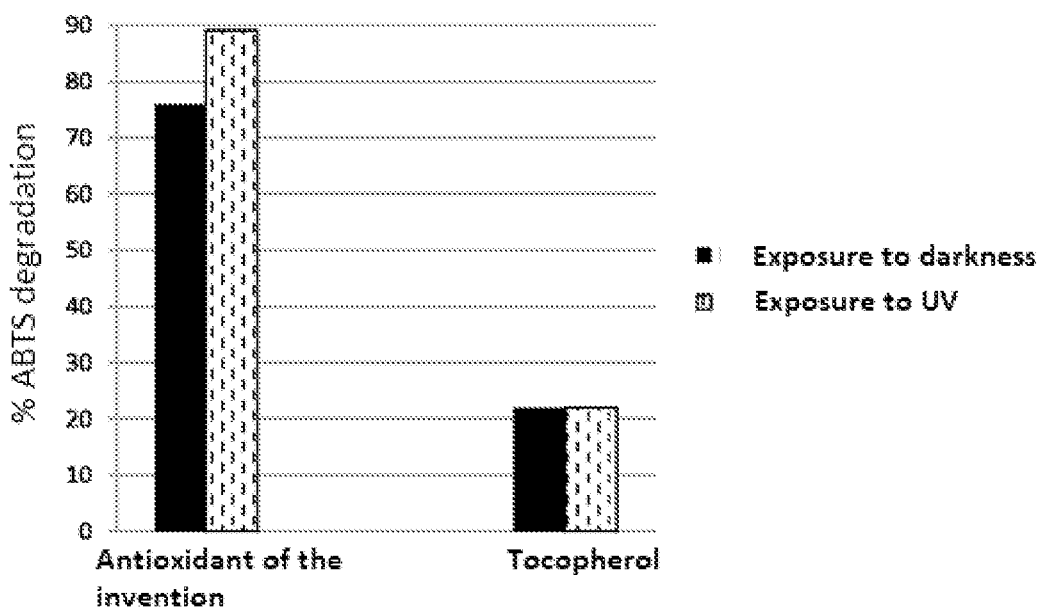
FIG. 4 shows the antioxidant activity of the colloids functionalized with the antioxidant (Col/AntiOx) of the invention compared with tocopherol, as placed in the dark or as exposed to UV.

The data is shown in FIG. 4.

The results show that the solution containing tocopherol had the same ABTS degradation capacity (22%) after exposure to UV or after exposure to the dark.

The solution containing ZnO/3-hydroxybenzaldehyde colloids and exposed to darkness had an ABTS degradation capacity that was very considerably greater than the tocopherol (76%). This activity was further increased after exposure to UV (89%).

In conclusion, the ZnO/3-hydroxybenzaldehyde colloids of the invention have an anti-radical activity that is more effective than a conventional antioxidant and a capacity to regenerate their antioxidant activity when they are exposed to UV radiation.

Example 6: Assessing the Antioxidant Activity of the Colloids Functionalized with Antioxidants (ZnO/3-hydroxybenzaldehyde) of the Invention The antioxidant activity of the ZnO/3-hydroxybenzaldehyde colloids was estimated by measuring the decomposition of 2,2-diphenyl-1-picrylhydrazyl (DPPH).

The results were expressed in $CI_{50}$ and/or in mg or µmol equivalent of the selected antioxidant sample. This method shows the capacity of a molecule to trap free radicals by transfer of electrons and/or of protons resulting from oxidation phenomenon. The protocol was as follows:
- an ethanol DPPH solution was prepared at 0.1 mM;
- the samples (antioxidant) to be tested were prepared at various masses lying in the range 4 mg to 40 mg;
- in a PMMA (poly(methyl methacrylate)) vessel, 3900 µL of solution of DPPH was mixed with 100 µL of sample to be tested. The reaction took place under incubation at ambient temperature, for 2 hours, and then absorbance at 515 nm was measured; and
- the percentage of antioxidant activity was plotted as a function of the concentration of the sample in question (in µM).

The percentage of antioxidant activity was determined using the following formula:

% antioxidant activity=$(A_{samp}/A_{blank})\times 100$ where $A_{samp}$ corresponds to the absorbance of the sample whereas $A_{blank}$ corresponds to the absorbance of a solution without any sample (100 µL of ethanol+3900 µL of a DPPH/ethanol solution).

The curve obtained has a linear portion and an asymptotic portion. The linear zone is in the form % AO=$\chi\times$[sample].

This formula makes it possible to determine the sample concentration that makes it possible to trap 50% of the radicals present, i.e. to determine the $CI_{50}$ in g/L (minimum concentration that is inhibiting at 50%) of the sample in question:

$CI_{50}=50/\chi$ where $\chi$ represents the slope of the linear regression line.

The antioxidant activity of the colloids of example 2 (ZnO/3-hydroxybenzaldehyde) was compared with that of conventional antioxidants listed below:
- Sample of 30 µL diluted to 0.5 g/L was placed in 2970 L of a solution at 0.07 mM of ABTS;
- Green tea extract containing over 40% of epigallocatechin gallate (EGCG);
- 87.3% of α-tocopherol+12.7% of soybean oil;
- 100% of L-ascorbic acid (Vitamin C); and
- 100% of propyl gallate.

Figure 5:
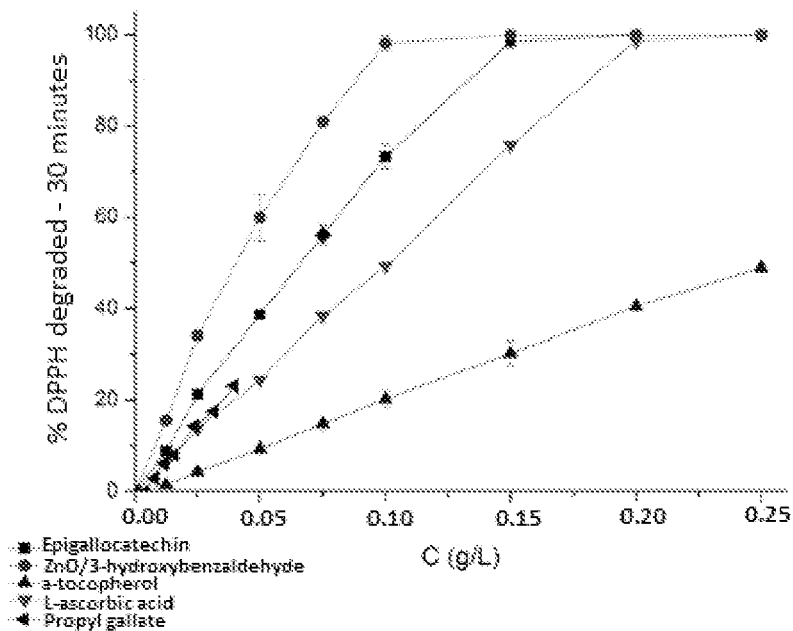
FIG. 5 shows the antioxidant activity of the colloids functionalized with an antioxidant (Col/AntiOx) of the invention compared with other antioxidants.

The results are shown in FIG. 5.

FIG. 5 shows that the colloids of the invention had a $CI_{50}$ of about 0.03 g/L, i.e. very considerably lower than those of conventional antioxidants. In other words, the concentration of ZnO/3-hydroxybenzaldehyde of the invention necessary for trapping 50% of the free radicals is less than that of conventional antioxidants.

Furthermore, an antioxidant activity greater than that of the other antioxidants at a concentration less than or equal to 0.15 g/L and similar at a concentration greater than 0.15 g/L was observed.

The antioxidant activity of ZnO/3-hydroxybenzaldehyde was thus greater than those of the other antioxidants tested.

Example 7: Assessing the Protective Power of the Composition of the Invention Against Generation of Primary and Secondary Free Radicals The trial was performed by the "spin trapping" method coupled with Electron Paramagnetic Resonance (EPR) for conducting trapping experiments in competition by using DIPPMPO (5-(Diisopropoxyphosphoryl)-5-methyl-1-pyrroline-N-oxide) as the trapping molecule. This compound is used conventionally for detecting and studying the superoxide radical using this technique.

The variation in the intensity of the signal of the adduct DIPPMPO-OOH was monitored as a function of time in the presence and in the absence of the creams. The method was assessed by studying the decomposition kinetics of a model radical (TEMPOL or 1-Oxyl-2,2,6,6-tetramethyl-4-hydroxypiperidine) in the presence and in the absence of creams. Over the duration of the trial, i.e. 20 minutes, no loss of signal from the TEMPOL was observed for the 4 experiments (control+3 samples). Also, control analyses in the presence of Superoxide Dismutase (SOD) were conducted.

TABLE 2

Percentage of inhibition of the DIPPMPO-OOH signal as a function of time.

| Cream | Inhibition at 3 minutes | Inhibition at 5 minutes | Inhibition at 10 minutes | Inhibition at 15 minutes |
|---|---|---|---|---|
| Sample A Complex of the invention (ZnO/3-hydroxybenzaldehyde) | 100% | 100% | 100% | 100% |
| Sample B Mixture of antioxidants: squalane + tocopherol acetate + magnesium ascorbyl phosphate | 48% | 50% | 45% | 53% |

TABLE 2-continued

Percentage of inhibition of the DIPPMPO-OOH signal as a function of time.

| Cream | Inhibition at 3 minutes | Inhibition at 5 minutes | Inhibition at 10 minutes | Inhibition at 15 minutes |
|---|---|---|---|---|
| Sample C Mixture of antioxidants : tocopherol acetate + tocopherol + ergothioneine | 20% | 23% | 37% | 44% |

The values indicated in the table are the means of 3 identical experiments (the fluctuations being less than 10%).

Figure 6:
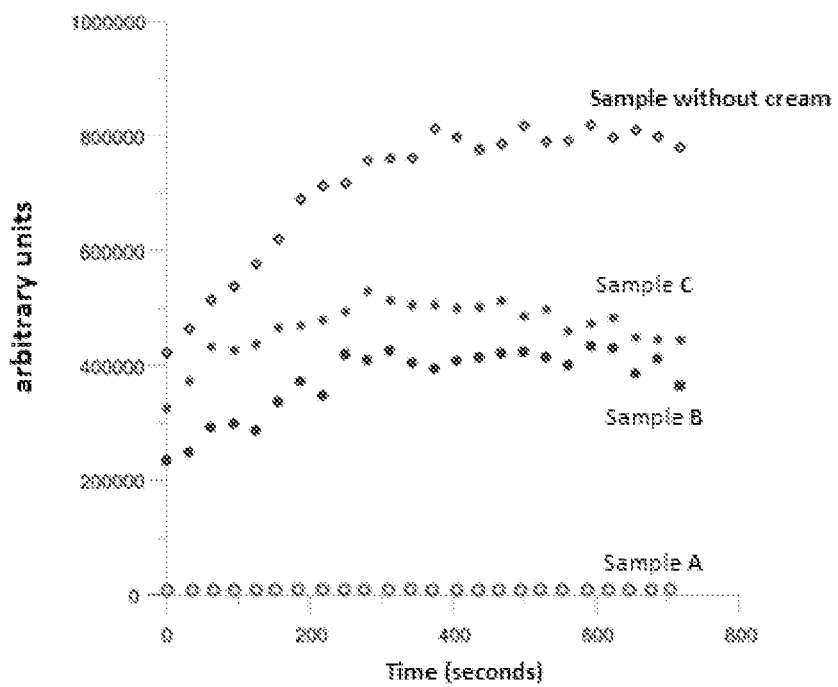
FIG. 6 shows the inhibition of any primary and/or secondary pro-oxidation activity of the colloids functionalized with the antioxidant (Col/AntiOx) of the invention compared with other antioxidants.

The inhibition kinetics are shown in FIG. 6.

Different superoxide radical trapping properties were observed for each sample.

Sample B showed a reduction of 48% at 3 minutes (53% at 5 minutes) in the signal of the DIPPMPO-OOH adduct, suggesting inhibition of half of the oxidizing activity.

Sample C showed a reduction of 20% at 3 minutes (44% at 5 minutes) in the signal of the DIPPMPO-OOH adduct, suggesting inhibition that was less effective than the inhibition of the sample B.

For the complex of the invention, i.e. sample A (the ZnO/3-hydroxybenzaldehyde colloids), no signal corresponding to the DIPPMPO-OOH adduct was observed. Thus, all of the superoxide radical produced was trapped.

During these experiments, formation of an additional radical was observed (except for the sample of the invention). According to the Applicant, it appeared that that new radical came from a Haber Weiss reaction or a Fenton reaction involving the presence of transition metal salts available for reacting with the superoxide radical or with the hydrogen peroxide (generated by spontaneous dismutation of the superoxide radical). Thus, the hydroxyl radical would appear to be generated and to react with the constituents of the cream to produce a new radical or "secondary radical", observed in the form of adduct on the DIPPMPO.

In conclusion, the colloids of the invention have capacity greater than the other compounds tested to trap free radicals of the superoxide type. Also, no production of secondary radical species was observed with the colloids of the invention, showing total effectiveness on inhibiting ROS and thus on inhibiting oxidative stress.

The invention claimed is:

1. Semiconductor colloids grafted covalently with an antioxidant, wherein the semiconductor colloids are colloids of zinc oxide, ZnO, and the antioxidant is 3-hydroxybenzaldehyde, wherein:

the 3-hydroxybenzaldehyde is grafted to the ZnO via a covalent bond between the aldehyde group of the 3-hydroxybenzaldehyde and atoms of the ZnO, or a spacer arm is positioned between the semiconductor colloid and the antioxidant, and is covalently bound to the 3-hydroxybenzaldehyde and the ZnO, wherein an alkoxysilane function of the spacer arm forms a covalent bond with atoms of the ZnO, wherein the semiconductor colloids regenerate antioxidant activity when exposed to radiation in the range 280 nm to 400 nm in the UV-A and UV-B range.

2. The colloids according to claim 1, wherein the spacer arm comprises in the range 1 to 8 carbons, and has an alkoxysilane function capable of binding itself covalently to the colloid and a function of the hydroxyl type, of the phosphate type, or of the amine type capable of binding itself to the antioxidant.

3. The colloids according to claim 2, wherein the spacer arm is 3-(Aminopropyl)triethoxysilane.

4. The colloids according to claim 1, wherein the 3-hydroxybenzaldehyde is grafted to the ZnO via a covalent bond between the aldehyde group of the 3-hydroxybenzaldehyde and atoms of the ZnO.

5. The colloids according to claim 1, wherein a spacer arm is positioned between the semiconductor colloid and the antioxidant, and is covalently bound to the 3-hydroxybenzaldehyde and the ZnO, wherein an alkoxysilane function of the spacer arm forms a covalent bond with atoms of the ZnO.

6. A topical composition comprising the colloids according to claim 1.

7. A topical composition according to claim 6, wherein it is devoid of any sun filters that are hydrophilic and/or lipophilic, inorganic and/or organic.

8. A topical composition according to claim 6, wherein it is in aqueous form, micellar form, or Pickering emulsion form.

9. A topical composition comprising the colloids according to claim 4.

10. A topical composition according to claim 9, wherein it is devoid of any sun filters that are hydrophilic and/or lipophilic, inorganic and/or organic.

11. A topical composition according to claim 9, wherein it is in aqueous form, micellar form, or Pickering emulsion form.

12. A topical composition comprising the colloids according to claim 5.

13. A topical composition according to claim 12, wherein it is devoid of any sun filters that are hydrophilic and/or lipophilic, inorganic and/or organic.

14. A topical composition according to claim 12, wherein it is in aqueous form, micellar form, or Pickering emulsion form.

15. A food supplement including colloids according to claim 1.

16. A food supplement including the colloids according to claim 4.

17. A food supplement including the colloids according to claim 5.

* * * * *